United States Patent
Tsujita (10) Patent No.: US 6,516,217 B1
(45) Date of Patent: Feb. 4, 2003

(54) FLUORESCENCE DIAGNOSIS SYSTEM

(75) Inventor: Kazuhiro Tsujita, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 226 days.

(21) Appl. No.: 09/613,596

(22) Filed: Jul. 10, 2000

(30) Foreign Application Priority Data

Jul. 9, 1999 (JP) ............................................ 11-195192

(51) Int. Cl.[7] ................................................. A61B 5/00
(52) U.S. Cl. .................................... 600/477; 250/461.2
(58) Field of Search ................................ 600/476, 477; 250/458.1, 461.2; 128/920

(56) References Cited

U.S. PATENT DOCUMENTS

| | | | |
|---|---|---|---|
| 5,042,494 A | * 8/1991 | Alfano | 600/477 |
| 5,507,287 A | 4/1996 | Palcic et al. | 128/633 |
| 5,579,773 A | 12/1996 | Vo-Dinh et al. | 128/665 |
| 5,647,368 A | * 7/1997 | Zeng et al. | 600/476 |
| 5,769,792 A | 6/1998 | Palcic et al. | 600/477 |
| 6,002,137 A | 12/1999 | Hayashi | 250/458.1 |
| 6,364,829 B1 | * 4/2002 | Fulghum | 600/160 |

FOREIGN PATENT DOCUMENTS

JP 10-225436 8/1998 ............ A61B/1/04

* cited by examiner

Primary Examiner—Shawna J Shaw
(74) Attorney, Agent, or Firm—Sughrue Mion, PLLC

(57) ABSTRACT

A fluorescence diagnosis system includes an exciting light projector which projects onto an organic part to be observed exciting light which is in a predetermined wavelength range suitable for exciting intrinsic fluorophore of the organic part to emit auto fluorescence. The intensity of the auto fluorescence emitted from the intrinsic fluorophore of the organic part to be observed upon excitation by the exciting light is detected. A plurality of characteristic values are obtained from the intensity of the auto. The condition of the organic part to be observed is recognized on the basis of the characteristic values in which the characteristic values comprise an intensity of the auto fluorescence and a normalized value of the intensity of the auto fluorescence, or a fluorescence yield of the auto fluorescence and a normalized value of the intensity of the auto fluorescence.

10 Claims, 8 Drawing Sheets

FLUORESCENCE DIAGNOSIS SYSTEM

BACKGROUND OF THE INVENTION

1. Field of the Invention

This invention relates to a fluorescence diagnosis system, and more particularly to a fluorescence diagnosis system in which the condition of a part of an organism to be diagnosed, e.g., change in the tissue condition of the part to be diagnosed, is recognized on the basis of auto fluorescence emitted from the tissue of the part to be diagnosed upon excitation by exciting light.

2. Description of the Related Art

There has been studied a fluorescence diagnosis system in which exciting light is projected onto a tissue of an organism, and auto fluorescence emitted from the tissue upon excitation by the exciting light is detected and analyzed, whereby change in the condition of the tissue caused by various diseases is recognized.

In the past, an attempt to recognize change in the tissue condition on the basis of change in intensity of the auto fluorescence was made. However since the intensity of the auto fluorescence has many sources of error and intensity information by itself does not sufficiently contribute to diagnosis, recently there have been made various attempts to recognize change in the tissue condition on the basis of the fact that the profile of spectral band intensities of the auto fluorescence changes with change in the tissue condition. For example, a diseased tissue greatly differs from a normal tissue in the ratio of intensity of a green region wavelength component of auto fluorescence to intensity of a red region wavelength component of the same. There has been proposed in Japanese Unexamined Patent Publication No. 6(1994)-54792 a fluorescence diagnosis system in which the ratio of intensity of a green region wavelength component to intensity of a red region wavelength component of auto fluorescence emitted from an organic tissue to be diagnosed is compared with that of an organic tissue which has been determined to be normal by a different system and whether the organic tissue to be diagnosed is diseased or normal is determined on the basis of the comparison. Further in the fluorescence diagnosis system disclosed in Japanese Unexamined Patent Publication No. 9(1997)-506027, intensities of auto fluorescence emitted from an organic tissue to be diagnosed at respective wavelengths are normalized with the intensity of the overall auto fluorescence (over the whole wavelength range) and made nondimensional, a difference curve is obtained by taking the difference between a profile curve of the nondimensional spectral band intensities and a similar profile curve for an organic tissue which has been determined to be normal by a different system (a reference profile curve), and whether the organic tissue to be diagnosed is diseased or normal is determined on the basis of the feature of the difference curve.

Further, we have proposed in Japanese Unexamined Patent Publication No. 10(1998)-225436 a fluorescence diagnosis system in which the intensity in a particular wavelength range of auto fluorescence emitted from an organic tissue to be diagnosed is normalized with the intensity of the overall auto fluorescence (over the whole wavelength range) and is compared with that of an organic tissue which has been determined to be normal by a different system, and whether the organic tissue to be diagnosed is diseased or normal is determined on the basis of comparison.

However, unlike a case where a sampled tissue is analyzed on a sample table by instruments, when living tissue is analyzed, the distance, angle and the like between the tissue and the part of the system from which the exciting light is projected onto the tissue and the auto fluorescence is received change from time to time. Accordingly characteristic of the detected auto fluorescence fluctuates, which makes it difficult to recognize change of the tissue condition (whether the tissue is normal or suffers from cancer, ulcer, inflammation, metaplasia or the like) at a reliable accuracy. Further the auto fluorescence also fluctuates depending on factors such as flow of blood which have little concern with the tissue condition. That is, since the auto fluorescence is very weak and includes various sources of error, it is very difficult to recognize change of a tissue at a high accuracy on the basis of a single characteristic value such as the intensity of the auto fluorescence or a normalized value of the intensity of the auto fluorescence.

SUMMARY OF THE INVENTION

In view of the foregoing observations and description, the primary object of the present invention is to provide a fluorescence diagnosis system which can recognize change of the part to be diagnosed at a high accuracy.

In accordance with the present invention, there is provided a fluorescence diagnosis system comprising an exciting light projecting means which projects onto an organic part to be observed exciting light which is in a predetermined wavelength range suitable for exciting intrinsic fluorophore of the organic part to emit auto fluorescence, a detecting means which detects the intensity of the auto fluorescence emitted from the intrinsic fluorophore of the organic part to be observed upon excitation by the exciting light, a characteristic value obtaining means which obtains a plurality of characteristic values from the intensity of the auto fluorescence detected by the detecting means, and a recognizing means which recognizes the condition of the organic part to be observed on the basis of the characteristic values.

For example, the characteristic values may comprise an intensity of the auto fluorescence and a normalized value of the intensity of the auto fluorescence, or a fluorescence yield of the auto fluorescence and a normalized value of the intensity of the auto fluorescence.

The normalized value of the intensity of the auto fluorescence may be obtained by dividing the intensity of a short wavelength component of the auto fluorescence by the intensity of the overall auto fluorescence.

For example, the recognizing means may recognize the condition of the organic part to be observed by making the characteristic values multivalued and executing a logical operation on the basis of the multivalued characteristic values.

Detection of the intensity of the auto fluorescence, obtaining the characteristic values and recognition of the condition of the organic part may be carried out pixel by pixel.

The expression "fluorescence yield" means the ratio of the intensity of the exciting light projected onto the organic part to be diagnosed to the intensity of the auto fluorescence emitted from the organic part exposed to the exciting light.

In accordance with the present invention, since the tissue condition of the organic part to be observed is recognized on the basis of a plurality of characteristic values obtained from the intensity of the auto fluorescence, the tissue condition can be recognized at a higher accuracy, irrespective of change of the auto fluorescence due to change in the distance, angle and the like between the tissue and the part of the system from which the exciting light is projected onto the tissue and the auto fluorescence is received or due to factors such as flow of blood which have little concern with the tissue condition, as compared with the conventional fluorescence diagnosis system where the tissue condition is recognized on the basis of a single characteristic value.

When the characteristic values comprise an intensity of the auto fluorescence and a normalized value of the intensity of the auto fluorescence, or a fluorescence yield of the auto fluorescence and a normalized value of the intensity of the auto fluorescence, the characteristic values can more properly reflect the tissue condition of the organic part and the tissue condition can be recognized at a further higher accuracy.

In this case, when the normalized value of the intensity of the auto fluorescence is obtained by dividing the intensity of a short wavelength component of the auto fluorescence by the intensity of the overall auto fluorescence, the characteristic values can further more properly reflect the tissue condition of the organic part and the tissue condition can be recognized at a further higher accuracy.

When the recognizing means recognizes the condition of the organic part to be observed by making the characteristic values multivalued and executing a logical operation on the basis of the multivalued characteristic value, the operation for recognizing the tissue condition is simplified and the time required to recognize the tissue condition is shortened.

DESCRIPTION OF THE PREFERRED EMBODIMENT

Figure 1:
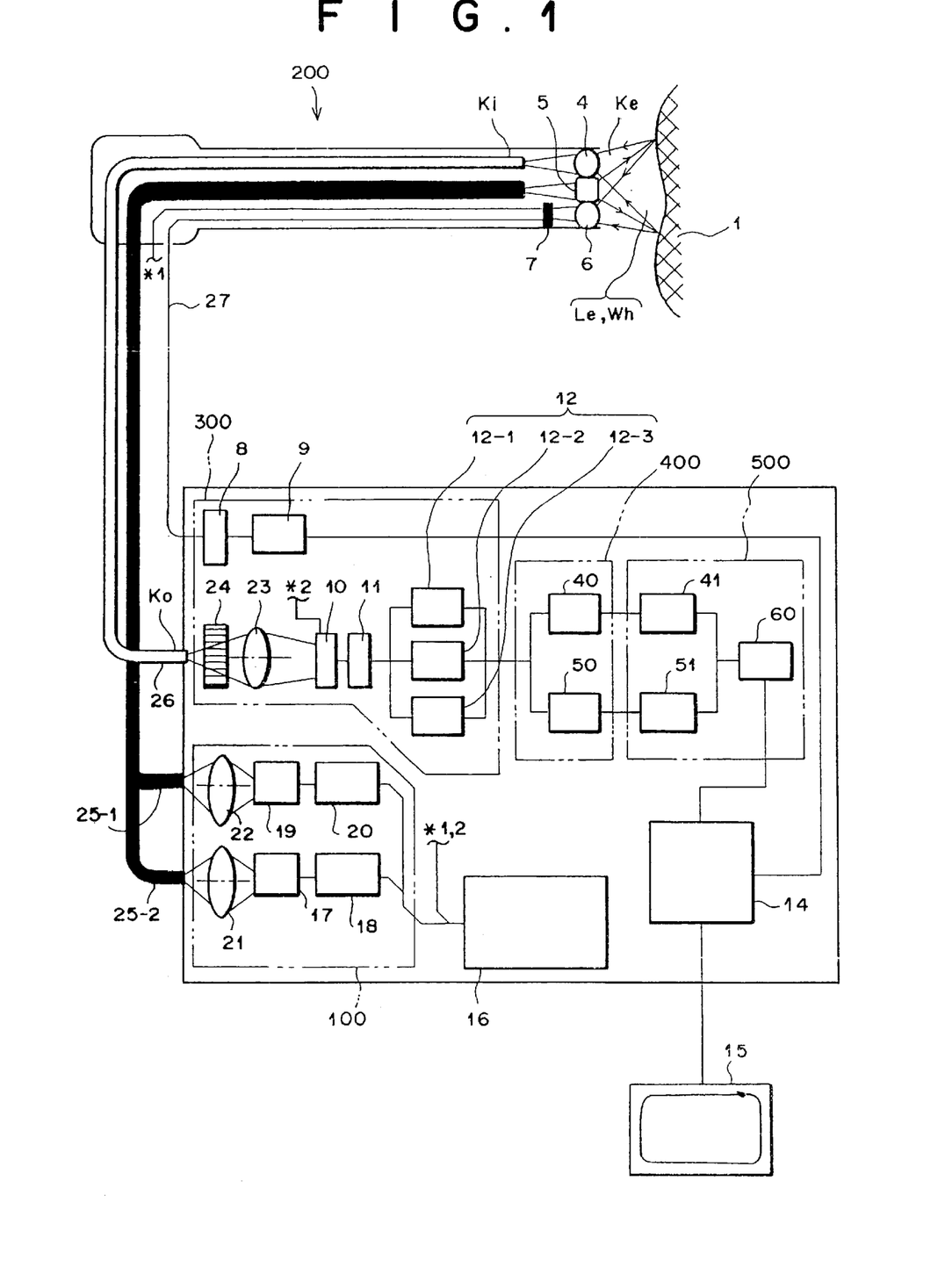
FIG. 1 is a schematic view showing a fluorescence endoscope in accordance with an embodiment of the present invention.

FIG. 1 shows a fluorescence endoscope as a fluorescence diagnosis system in accordance with an embodiment of the present invention.

As shown in FIG. 1, the fluorescence endoscope comprises a light source section 100 having a white light source 19 and an exciting light source 17, and a flexible front end portion 200 which leads white light Wh and exciting light Le to an organic part 1 and takes a normal image of the organic part 1 formed by the white light Wh while propagating an auto fluorescence image formed by auto fluorescence emitted from the organic part 1 upon excitation by the exciting light. The normal image taken by the front end portion 200 is taken in by an image take-in section 300. The image take-in section 300 takes in the normal image as image data and stores the image data. Further, the image take-in section 300 receives the fluorescence image, divides the fluorescence image into three wavelength ranges and stores the three pieces of image data corresponding to the three wavelength ranges. A characteristic obtaining means 400 obtains two pieces of image data corresponding to a pair of characteristic values from the pieces of image data stored by the image take-in section 300. The two pieces of image data obtained by the characteristic obtaining means 400 is input into a recognizing section 500 and the recognizing section 500 carries out a logical operation for recognizing change of the tissue condition due to a disease on the basis of the two pieces of image data and outputs the result of the operation as a piece of image data. The image data output from the recognizing section 500 is input into a video signal processing circuit 14 together with the normal image data stored in the image take-in section 300 and the video signal processing circuit 14 converts the two pieces of image data into a video signal and outputs the video signal to a display section 15. A control section 16 controls projection of the exciting light Le, projection of the white light Wh, reading of the normal image, reading of the fluorescence image, and the like.

The white light source 19 of the light source section 100 is connected to a power source 20 which is controlled by the control section 16. The white light source 19 is energized to emit the white light Wh in a cycle of a 1/60 second and the white light Wh is condensed by a white light condenser lens 22 and introduced into a white light guide 25-1 which is formed of multi-component glass optical fiber and connected to the light source section 100.

The exciting light source 17 comprises a semiconductor laser and driven by an LD power source 18, which is controlled by the control section 16, to generate pulse-like exciting light Le at about 410 nm in a cycle of a 1/60 second. The exciting light Le is condensed by an exciting light condenser lens 21 and introduced into an exciting light guide 25-2 which is formed of silica optical fiber and connected to the light source section 100.

The white light guide 25-1 and the exciting light guide 25-2 are bundled into a cable.

The cable of the white light guide 251-1 and the exciting light guide 25-2 extends through the front end portion 200 and is provided with an illumination lens 5 at the front end thereof. The white light Wh and the exciting light Le respectively emitted from the white light guide 25-1 and the exciting light guide 25-2 are projected onto the organic part 1 through the illumination lens 5. A normal image of the organic part 1 illuminated by the white light Wh is formed on a light receiving surface of a normal image taking CCD device 7 by a normal image objective lens 6 and converted to an electric image signal by the CCD device 7. The image signal representing the normal image of the organic part 1 is transferred to the image take-in section 300 through a CCD cable 27. An image formed by fluorescence Ke emitted from the organic part 1 upon excitation by the exciting light Le is formed on an end face Ki of a fluorescence image optical fiber 26 by a fluorescence image objective lens 4 and the fluorescence image propagates through the fluorescence image optical fiber 26 to the other end face Ko of the fluorescence image optical fiber 26 connected to the image take-in section 300.

The image take-in section 300 is provided with a normal A/D converter 8 which digitizes the electric image signal representing the normal image of the organic part 1 and a normal image memory 9 which stores the digitized image signal. The image take-in section 300 is further provided with an optical system which takes in the fluorescence image, propagating to the end face Ko of the fluorescence image optical fiber 26 through an exciting light cut filter 24 which cuts light of a wavelength not longer than about 410 nm, and forms a fluorescence image on a light receiving face of a high-sensitive image taking device 10 through a fluorescence condenser lens 23, an A/D converter 11 which digitizes an electric image signal obtained by converting the fluorescence image by the high-sensitive image taking device 10 and a fluorescence image memory means 12 which stores the digitized image signal representing the fluorescence image.

Figure 2:
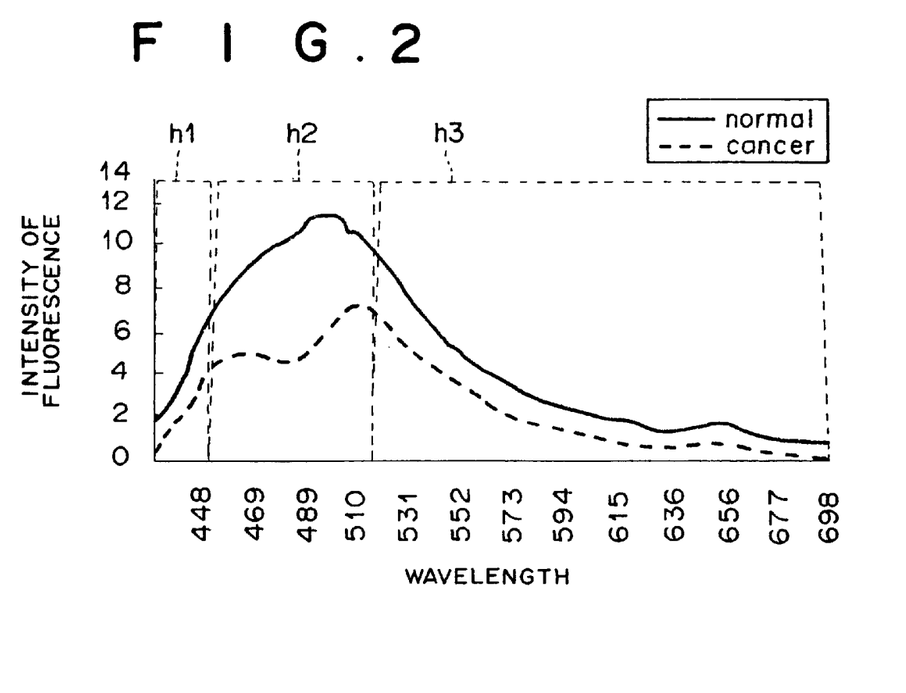
FIG. 2 is a view showing examples of fluorescence spectrum of a normal tissue and a cancered tissue.
Figure 3:
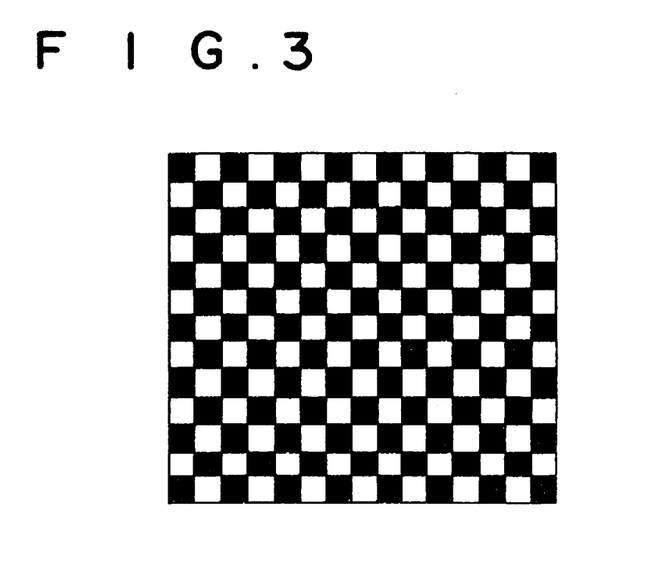
FIG. 3 is a view showing the mosaic filter.

The light receiving face of the high-sensitive image taking device 10 is covered with a color mosaic filter shown in FIG. 3 which is an integrated body of three different filters one of which transmits only light in a wavelength range h1 (from about 430 nm to about 445 nm), another of which transmits only light in a wavelength range h2 (from about 445 nm to about 520 nm), and the other of which transmits only light in a wavelength range h3 (from about 520 nm to about 700 nm) as shown in FIG. 2. By virtue of the color mosaic filter, the fluorescence image is divided into the three wavelength ranges h1 to h3, and the intensity of the fluorescence in the wavelength range h1 is digitized and stored in a first memory 12-1 of the fluorescence image memory means 12, the intensity of the fluorescence in the wavelength range h2 is digitized and stored in a second memory 12-2, and the intensity of the fluorescence in the wavelength range h3 is digitized and stored in a third memory 12-3.

The characteristic obtaining means 400 comprises a first characteristic value output means 40 which obtains fluorescence intensity image data ZK representing the intensity of the overall fluorescence (over the whole wavelength range) on the basis of the three pieces of intensity data stored in the first to third memories 12-1 to 12-3, and outputs the fluorescence intensity image data ZK as a first characteristic value. The characteristic obtaining means 400 further comprises a second characteristic value output means 50 which obtains normalized fluorescence intensity image data KK by normalizing the intensity of the fluorescence in the wavelength range h2 with the intensity of the overall fluorescence (dividing the former by the latter) and outputs the normalized fluorescence intensity image data KK as a second characteristic value.

As shown in FIG. 2, a diseased tissue is generally weaker than a normal tissue in the intensity of the overall auto fluorescence (over the whole wavelength range) and differs from a normal tissue in profile of spectral band intensities in the wavelength range h2. As will become apparent later, the fluorescence intensity image data ZK (the first characteristic value) directly or indirectly reflects the intensity of the overall auto fluorescence, whereas the normalized fluorescence intensity image data KK (the second characteristic value) directly or indirectly reflects the profile of the spectral band intensities of the auto fluorescence in the wavelength range h2. The intensity of the overall fluorescence may be considered to be the sum of intensities of the fluorescence in the respective wavelength bands h1 to h3.

The recognizing section 500 comprises a first binary-coding means 41 which binary-codes the fluorescence intensity image data ZK output from the first characteristic value output means 40 by the use of a threshold value ZS for the intensity of the overall fluorescence, which has been stored therein, and outputs binary-coded fluorescence intensity image data ZN, and a second binary-coding means 51 which binary-codes the normalized fluorescence intensity image data KK output from the second characteristic value output means 50 by the use of a threshold value KS for the intensity of the normalized intensity of the fluorescence, which has been stored therein, and outputs binary-coded normalized fluorescence intensity image data KN. The recognizing section 500 further comprises a logical operator 60 which executes a logical operation on the basis of the binary-coded fluorescence intensity image data ZN and the binary-coded normalized fluorescence intensity image data KN and outputs the result of the operation as a fluorescence diagnosis image data KSG.

Operation of the fluorescence endoscope of this embodiment will be described with reference to the timing chart shown in FIG. 4, hereinbelow.

Figure 4:
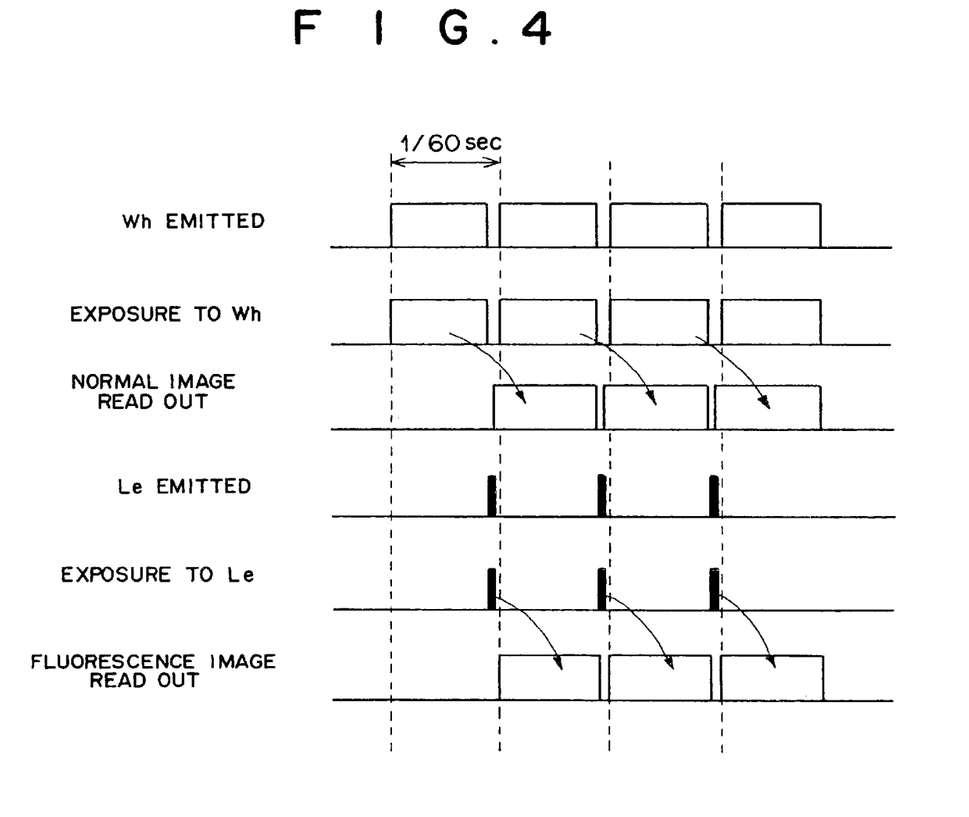
FIG. 4 is a flow chart illustrating the timings of taking normal images and fluorescence images.

The fluorescence endoscope of this embodiment is controlled by the control section 16 according to the timing chart shown in FIG. 4. The white light Wh emitted from the white light source 19 in a period of a 1/60 second is led to the white light guide 25-1, propagates through the white light guide 25-1 and illuminates the organic part 1 through the illumination lens 5. An image of the organic part 1 illuminated by the white light Wh is formed on the light receiving face of the normal image taking CCD device 7 by the normal image objective lens 6, and stored in the normal image taking CCD device 7 as signal charges. Then in the next period of a 1/60 second, an electric-image signal representing the normal image of the organic part 1 is read out from the CCD device 7 and is digitized by the A/D converter 8. The digital image signal thus obtained is stored in the normal image memory 9.

In the period, after the end of projection of the white light Wh, pulse-like exciting light Le is emitted from the exciting light source 17 and is projected onto the organic part 1 through the exciting light condenser lens 21, the exciting light guide 25-2 and the illumination lens 5.

Fluorescence Ke emitted from the organic part 1 upon excitation by the exciting light Le is caused to form an image on the end face Ki of the fluorescence image optical fiber 26 by the fluorescence image objective lens 4 and the fluorescence image is propagated through the fluorescence image optical fiber 26 to the other end face Ko. The fluorescence image is then focused on the light receiving face of the high-sensitive image taking device 10 through the exciting light cut filter 24 and the mosaic filter with the exciting light contained in the fluorescence image removed by the cut filter 24, and is stored in the image taking deice 10 as signal charges. Then in the next period of a 1/60 second, an electric image signal representing the fluorescence image is read out from the image taking device 10 and is digitized by the A/D converter 11. The digital image signal thus obtained is stored in the fluorescence image memories 12-1, 12-2 and 12-3.

As can be seen from FIG. 4, the normal image and the fluorescence image are taken every 1/60 second, and the white light Wh and the exciting light Le are projected onto the organic part at different timings in each period of a 1/60 second.

The digital fluorescence image signals stored in the respective memories 12-1, 12-2 and 12-3 are then input into the first and second characteristic value output means 50.

Figure 5A:
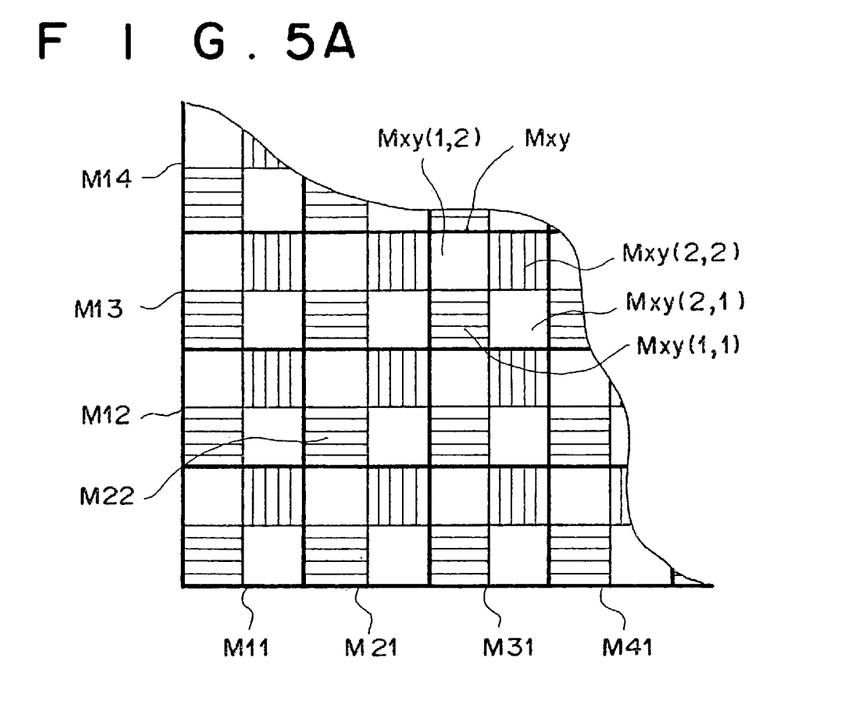
FIG. 5A is an enlarged view of the mosaic filter.
Figure 5B:
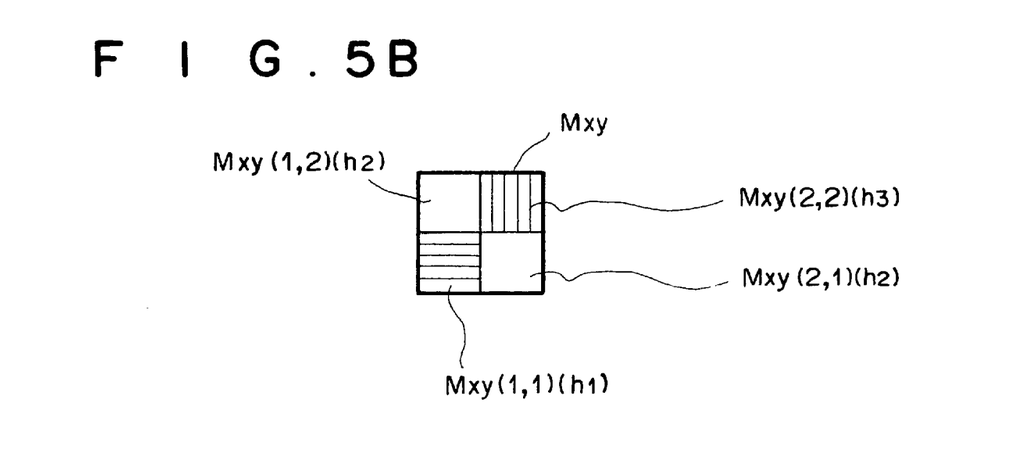
FIG. 5B is an enlarged view of one micro-segment of the mosaic filter.

As shown in an enlarged scale in FIG. 5A, the mosaic filter on the high-sensitive image taking device 10 comprises a number of micro-segments Mxy (x stands for the number of the column as numbered from the leftmost column and y stands for the number of the lines as number from the lowermost line) arranged in a matrix pattern. As shown in FIG. 5B, each micro-segment Mxy comprises four square filters Mxy(1,1), Mxy(2,1), Mxy(2,2) and Mxy(1,2). The filter Mxy(1,1) transmits only light in a wavelength range h1 (from about 430 nm to about 445 nm), the filters Mxy(2,1) and Mxy(1,2) transmit only light in a wavelength range h2 (from about 445 nm to about 520 nm), and the filter Mxy(2,2) transmits only light in a wavelength range h3 (from about 520 nm to about 700 nm). When intensities of fluorescence passing through the respective filters Mxy(1,1), Mxy(2,1), Mxy(2,2) and Mxy(1,2) of one micro-segment Mxy are represented by Dxy(1,1), Dxy(2,1), Dxy(2,2) and Dxy(1,2), the value of the fluorescence intensity image data ZKxy for the micro-segment Mxy representing the intensity of the fluorescence over the whole wavelength range passing at the micro-segment Mxy is obtained by the following formula.

$$ZKxy=[\{Dxy(1,2)+Dxy(2,1)\}/2+Dxy(1,1)+Dxy(2,2)]$$

The normalized fluorescence intensity image data KKxy for the micro-segment Mxy representing the value obtained by dividing the intensity of the fluorescence in the wavelength h2 by the intensity of the overall fluorescence ZKxy is obtained by the following formula.

$$KKxy=[\{Dxy(1,2)+Dxy(2,1)\}/2]/[\{Dxy(1,2)+Dxy(2,1)\}/2+Dxy(1,1)+Dxy(2,2)]$$

By obtaining the value of the fluorescence intensity image data ZKxy and the normalized fluorescence intensity image data KKxy for all the micro-segments (M11, M12, M13, M14 . . . ) in this manner, the fluorescence intensity image data ZK and the normalized fluorescence intensity image data KK are obtained for the fluorescence image signal of the organic part 1. The first characteristic value output means 40 calculates the fluorescence intensity image data ZK on the basis of the image signals stored in the memories 12-1 to 12-3 and outputs calculated fluorescence intensity image data ZK to the recognizing section 500 and the second characteristic value output means 50 calculates the normalized fluorescence intensity image data KK on the basis of the image signals stored in the memories 12-1 to 12-3 and outputs calculated normalized fluorescence intensity image data KK to the recognizing section 500.

The first binary-coding means 41 binary-codes the fluorescence intensity image data ZK output from the first characteristic value output means 40 by the use of a threshold value ZS for the intensity of the overall fluorescence, which has been stored therein, and outputs binary-coded fluorescence intensity image data ZN to the logical operator 60, and the second binary-coding means 51 binary-codes the normalized fluorescence intensity image data KK output from the second characteristic value output means 50 by the use of a threshold value KS for the normalized intensity of the fluorescence, which has been stored therein, and outputs binary-coded normalized fluorescence intensity image data KN to the logical operator 60.

Figure 6A:
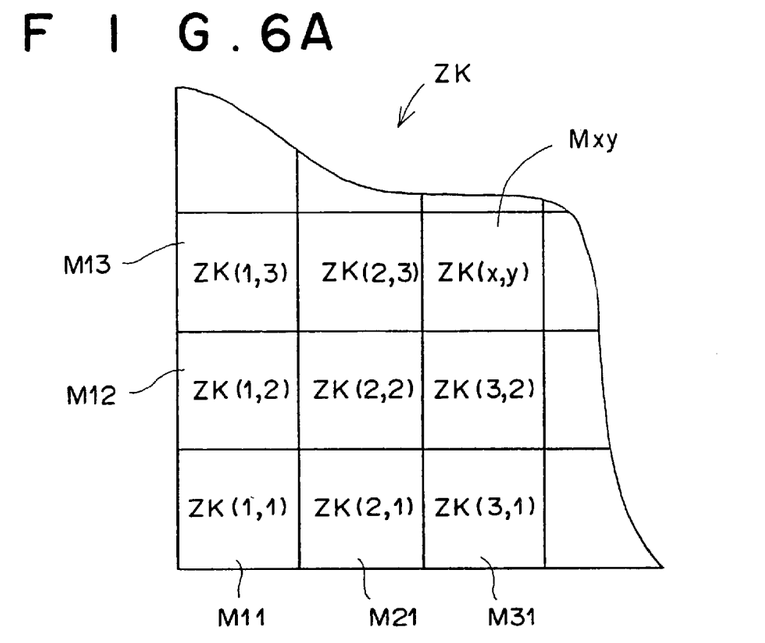
FIG. 6A is a fragmentary view showing an example of the fluorescence intensity image data.
Figure 6B:
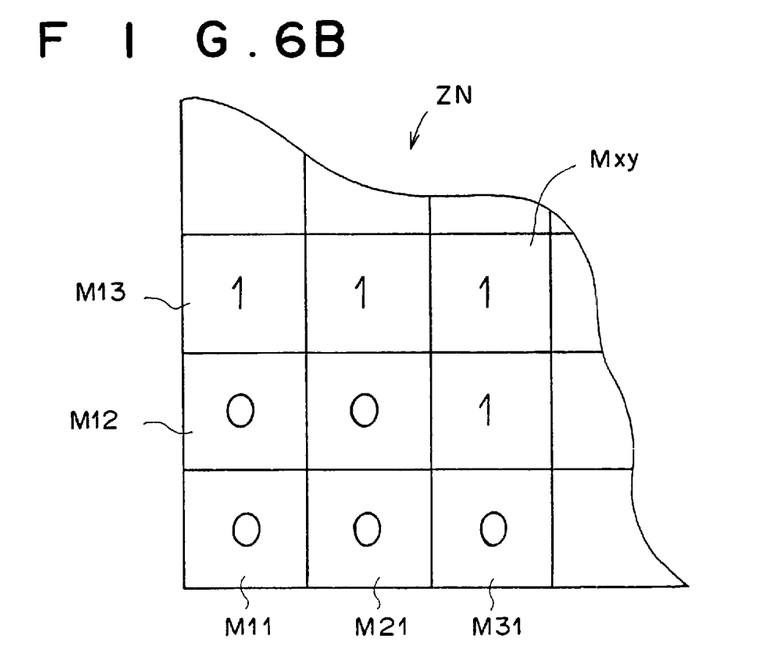
FIG. 6B is a fragmentary view showing the binary-coded fluorescence intensity image data.

The first binary-coding means 41 binary-codes the fluorescence intensity image data ZK and obtains the binary-coded fluorescence intensity image data ZN in the following manner. That is, as shown in FIGS. 6A and 6B, when the value of the fluorescence intensity image data ZK for a micro-segments Mxy satisfies the following formula, the first binary-coding means 41 converts the value of the fluorescence intensity image data ZK to 1, fluorescence intensity image data ZK≧threshold value ZS, and when the value of the fluorescence intensity image data ZK for the micro-segments Mxy satisfies the following formula, the first binary-coding means 41 converts the value of the fluorescence intensity image data ZK to 0, fluorescence intensity image data ZK<threshold value ZS.

Figure 7A:
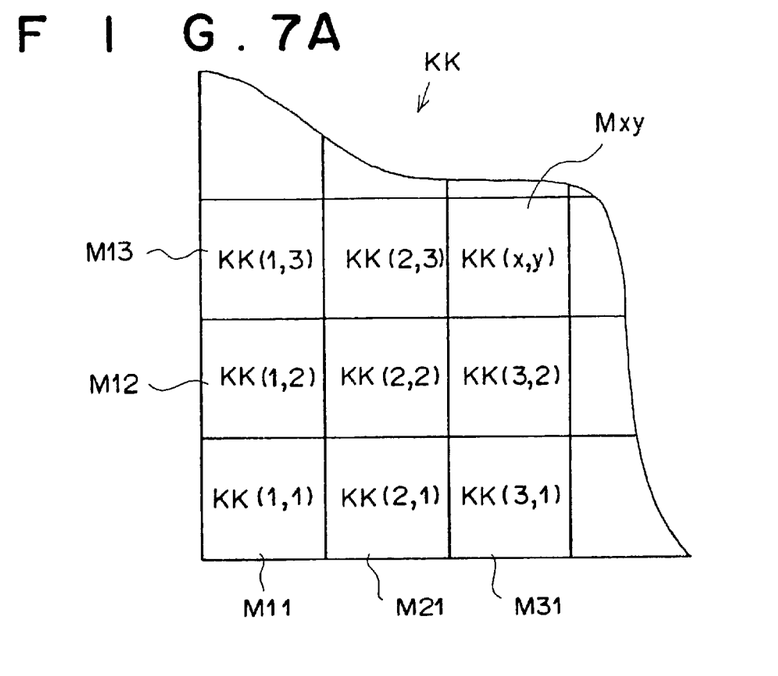
FIG. 7A is a fragmentary view showing an example of the normalized fluorescence intensity image data.
Figure 7B:
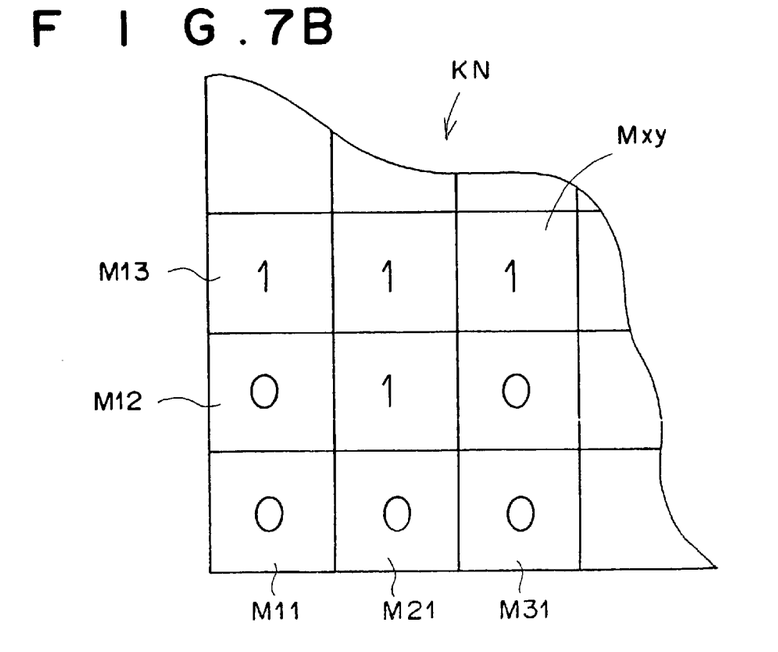
FIG. 7B is a fragmentary view showing the binary-coded normalized fluorescence intensity image data.

The second binary-coding means 51 binary-codes the normalized fluorescence intensity image data KK and obtains the binary-coded normalized fluorescence intensity image data KN in the following manner. That is, as shown in FIGS. 7A and 7B, when the value of the normalized fluorescence intensity image data KK for a micro-segments Mxy satisfies the following formula, the second binary-coding means 51 converts the value of the normalized fluorescence intensity image data KK to 1, normalized fluorescence intensity image data KK≧threshold value KS, and when the value of the normalized fluorescence intensity image data KK for the micro-segments Mxy satisfies the following formula, the second binary-coding means 51 converts the value of the normalized fluorescence intensity image data KK to 0, normalized fluorescence intensity image data KK <threshold value KS.

The threshold value ZS for the intensity of the overall fluorescence is a value obtained by subtracting a standard deviation σ from an average Zav of a number of pieces of fluorescence intensity image data ZK calculated for an organic tissue which has been determined to be normal (ZS=Zav−σ). The threshold value KS for the normalized intensity of the fluorescence is a value obtained by subtracting a standard deviation σ from an average Kav of a number of pieces of normalized fluorescence intensity image data KK calculated for an organic tissue which has been determined to be normal (KS=Kav−σ).

Accordingly, the micro-segments where the fluorescence intensity image data ZK is not smaller than the threshold value ZS and the binary-coded fluorescence intensity image data ZN is 1 correspond to the parts of the organic part 1 which can be determined to be normal on the basis of the intensity of the overall fluorescence, whereas the micro-segments where the fluorescence intensity image data ZK is smaller than the threshold value ZS and the binary-coded fluorescence intensity image data ZN is 0 correspond to the parts of the organic part 1 which cannot be determined to be normal on the basis of the intensity of the overall fluorescence. Similarly, the micro-segments where the normalized fluorescence intensity image data KK is not smaller than the threshold value KS and the binary-coded normalized fluorescence intensity image data KN is 1 correspond to the parts of the organic part 1 which can be determined to be normal on the basis of the normalized fluorescence intensity image data, whereas the micro-segments where the normalized fluorescence intensity image data KK is smaller than the threshold value KS and the binary-coded normalized fluorescence intensity image data KN is 0 correspond to the parts of the organic part 1 which cannot be determined to be normal on the basis of the normalized fluorescence intensity image data.

Figure 8A:
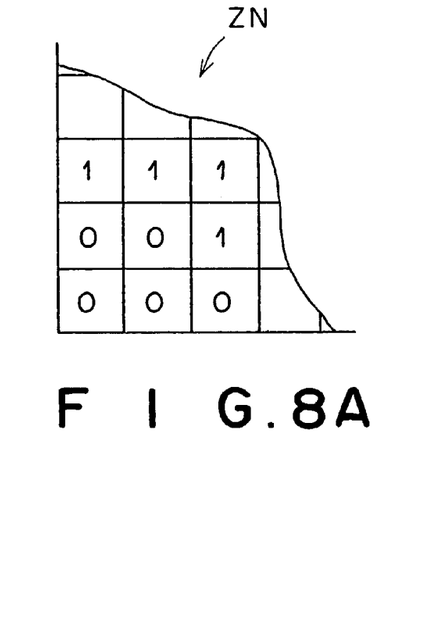
FIGS. 8A to 8D are views for illustrating the logical operation.
Figure 8B:
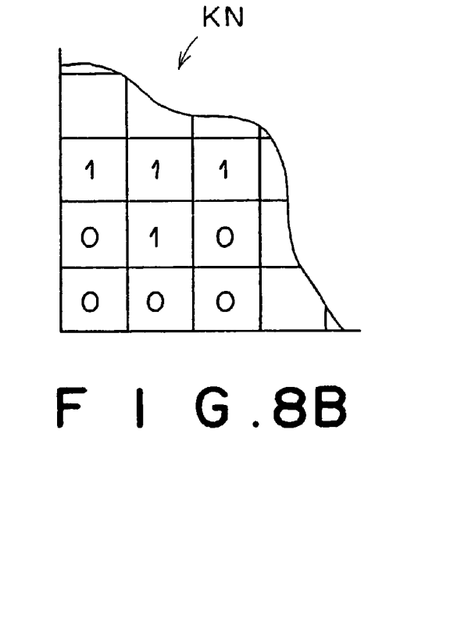
Figure 8C:
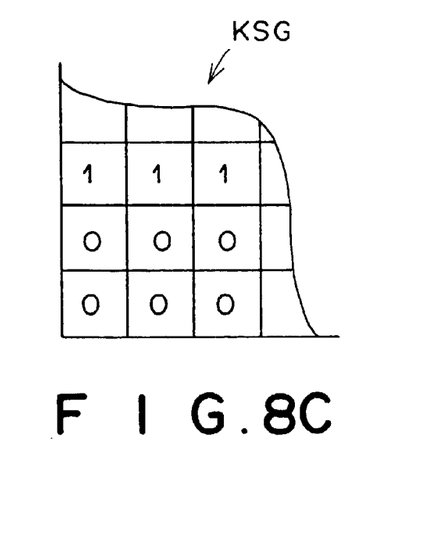
Figure 8D:
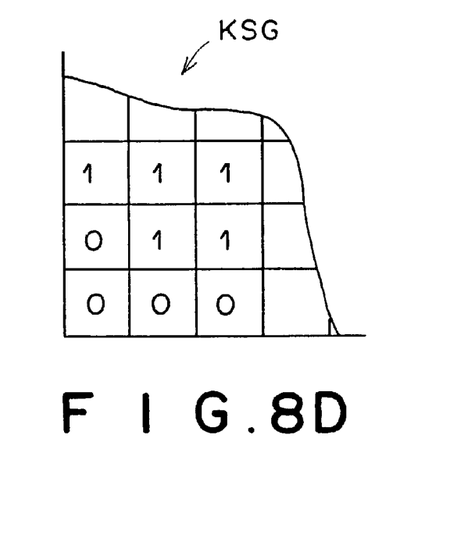

The binary-coded fluorescence intensity image data ZN and the binary-coded normalized fluorescence intensity image data KN are input into the logical operator 60. The logical operator 60 carries out a logical operation on the basis of the binary-coded fluorescence intensity image data ZN and the binary-coded normalized fluorescence intensity image data KN pixel by pixel with the pixels of the binary-coded fluorescence intensity image data ZN and the binary-coded normalized fluorescence intensity image data KN matched with each other and outputs the result of the operation as a fluorescence diagnosis image data KSG. That is, when a normal part of the organic part 1 is to be recognized, the logical operator 60 takes a logical product of the binary-coded fluorescence intensity image data ZN for each pixel and the binary-coded normalized fluorescence intensity image data KN for the corresponding pixel, and determines whether the part of the organic part 1 corresponding to the pixel is normal according to the value of the logical product (KSG). That is, when the logical product KSG is 1, the part of the organic part 1 corresponding to the pixel is recognized to be normal, whereas when the logical product KSG is 0, it is determined that the part of the organic part 1 corresponding to the pixel can be diseased. Assuming that the binary-coded fluorescence intensity image data ZN and the binary-coded normalized fluorescence intensity image data KN are respectively as shown in FIGS. 8A and 8B, the logical products KSG of the binary-coded fluorescence intensity image data ZN and the binary-coded normalized fluorescence intensity image data KN are as shown in FIG. 8C. When a diseased part of the organic part 1 is to be recognized, the logical operator 60 takes a logical sum of the binary-coded fluorescence intensity image data ZN for each pixel and the binary-coded normalized fluorescence intensity image data KN for the corresponding pixel, and determines whether the part of the organic part 1 corresponding to the pixel is diseased according to the value of the logical sum (KSG). That is, when the logical sum KSG is 0, the part of the organic part 1 corresponding to the pixel is recognized to be diseased, whereas when the logical sum KSG is 1, it is determined that the part of the organic part 1 corresponding to the pixel can be normal. Assuming that the binary-coded fluorescence intensity image data ZN and the binary-coded normalized fluorescence intensity image data KN are respectively as shown in FIGS. 8A and 8B, the logical sums KSG of the binary-coded fluorescence intensity image data ZN and the binary-coded normalized fluorescence intensity image data KN are as shown in FIG. 8D.

In order to prove the accuracy in recognizing the tissue condition of the fluorescence endoscope, the following experiments were effected.

Auto fluorescence emitted from 82 points of 17 different organic tissues were detected and whether each of the 82 points was normal or diseased was determined in the manner described above. In this experiment, auto fluorescence emitted from the organic tissues were detected as points rather than as an image. The condition of the 17 organic tissues, that is, whether they were normal or diseased, had been known in advance.

The aforesaid two characteristic values, i.e., fluorescence intensity data and normalized fluorescence intensity data, were obtained for each of the 82 points and binary-coded in the manner described above, whereby binary-coded fluorescence intensity data ZN1 and binary-coded normalized fluorescence intensity data KN1 were obtained for each point. Then the logical product of the binary-coded fluorescence intensity data ZN1 and binary-coded normalized fluorescence intensity data KN1 were taken for each point. The logical products for 23 points were 1, that is, the 23 points were determined to be normal. However, actually, 5 of the 23 points were diseased. Accordingly, the recognizing accuracy was $\{(23-5)/23\} \times 100 \approx 78\%$. Similarly, the logical sum of the binary-coded fluorescence intensity data ZN1 and binary-coded normalized fluorescence intensity data KN1 were taken for each point. The logical sum for 31 points were 0, that is, the 31 points were determined to be diseased. However, actually, 7 of the 31 points were normal. Accordingly, the recognizing accuracy was $\{(31-7)/31\} \times 100 \approx 77\%$.

To the contrast, when the normal tissue was distinguished from the aforesaid 82 points by use of only the normalized fluorescence intensity data (only one characteristic value) as in the conventional system, that is, when the points where the normalized fluorescence intensity data is not smaller than the threshold value KS for the intensity of the normalized intensity of the fluorescence were recognized to be normal, 52 points were determined to be normal. However, actually, 23 of the 52 points were diseased. Accordingly, the recognizing accuracy was $\{(52-23)/52\} \times 100 \approx 55\%$.

This difference is sufficiently significant.

The experiment described above will be described more specifically assuming that the points were ten in number.

Figure 9A:
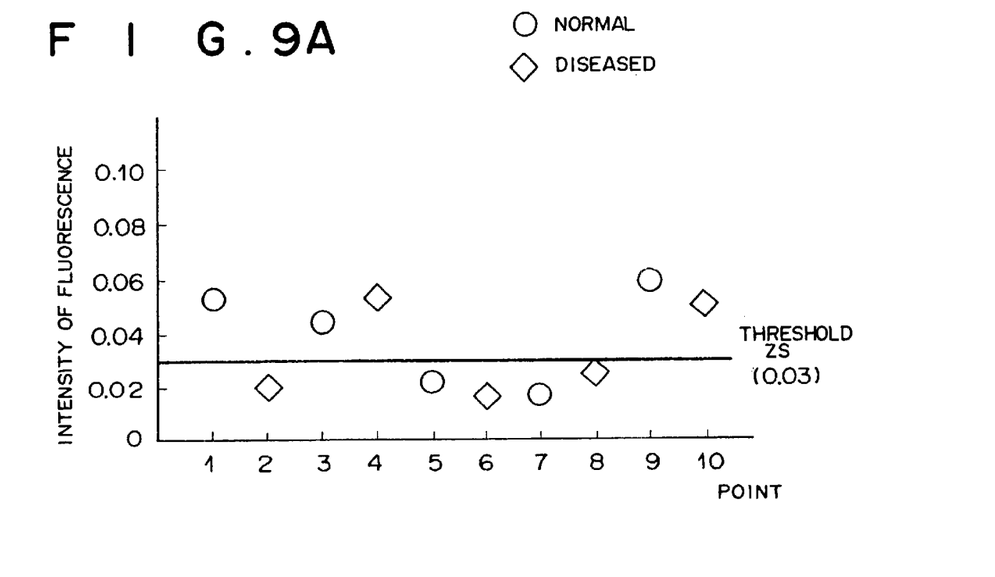
FIGS. 9A and 9B are views for illustrating the experiment for proving the effect of the present invention.
Figure 9B:
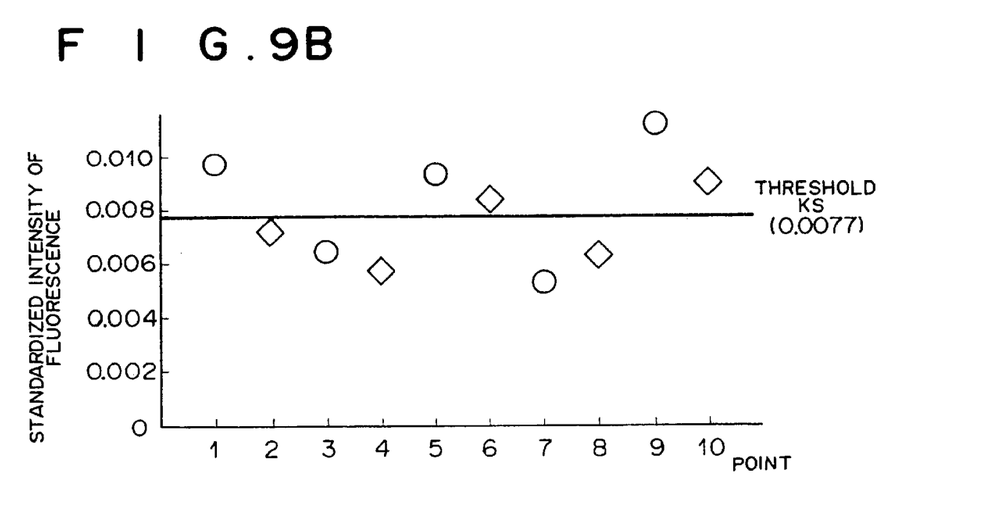

As shown in FIGS. 9A and 9B, it had been known that points 1, 3, 5, 7 and 9 were diseased and points 2, 4, 6, 8 and 10 were normal. The fluorescence intensity data and the normalized fluorescence intensity data were obtained for each of the 10 points. When which of the 10 points were normal was determined on the basis solely of comparison of the intensity of fluorescence and the threshold value ZS, points 1, 3, 4, 9 and 10 were determined to be normal whereas points 2, 5, 6, 7 and 8 were not determined to be normal. On the other hand, when which of the 10 points were normal was determined on the basis solely of comparison of the normalized intensity of fluorescence and the threshold value KS, points 1, 5, 6, 9 and 10 were determined to be normal whereas points 2, 3, 4, 7 and 8 were not determined to be normal.

When normal tissues are to be recognized on the basis of both the intensity of fluorescence and the normalized intensity of fluorescence, the points common to the points determined to be normal by comparison of the intensity of fluorescence and the threshold value ZS and those determined to be normal by comparison of the normalized intensity of fluorescence and the threshold value KS, that is, points 1, 9 and 10, are determined to be normal. However, since point 10 has been known to be diseased, determination for one point out of three points is erroneous. Accordingly, the recognizing accuracy is $\{(3-1)/3\} \times 100 \approx 66\%$. Similarly, when diseased tissues are to be recognized, the points common to the points not determined to be normal by comparison of the intensity of fluorescence and the threshold value ZS and those not determined to be normal by comparison of the normalized intensity of fluorescence and the threshold value KS, that is, points 2, 7 and 8, are determined to be diseased. However, since point 7 has been known to be normal, determination for one point out of three points is erroneous. Accordingly, the recognizing accuracy is $\{(3-1)/3\} \times 100 \approx 66\%$.

The fluorescence diagnosis image data KSG obtained in the manner described above is input into the video signal processing circuit 14 together with the normal image data output from the normal image memory 9 and the fluorescence diagnosis image data KSG and the normal image data are processed so that an image represented by the normal image data and an image represented by the fluorescence diagnosis image data KSG are simultaneously displayed in one frame and input into the display section 15.

In place of the intensity of the overall auto fluorescence (the sum of the intensities of the fluorescence in the wavelength ranges h1, h2 and h3 in the embodiment described above), a fluorescence yield of the auto fluorescence may be employed as a characteristic value.

Though the fluorescence yield is basically a ratio between the intensity of the exciting light projected onto the organic part to be diagnosed to the intensity of the auto fluorescence emitted from the organic part exposed to the exciting light, any value may be employed in place of the intensity of the exciting light projected onto the organic part so long as it is proportional to the intensity of the exciting light projected onto the organic part. For example, the intensity of exciting light reflected at the organic part, the intensity of near infrared rays emitted from another light source which emits near infrared rays in the same intensity as the exciting light, or the intensity of near infrared rays which is emitted from another light source which emits near infrared rays in the same intensity as the exciting light and reflected at the organic part may be employed.

That is, the value of the fluorescence yield and the value of the normalized intensity of fluorescence can be obtained, for instance, in the following manner. A semiconductor laser emitting an exciting laser beam at about 410 nm and a light source emitting a near infrared beam, such as semiconductor laser, LED or SLD are provided in place of the exciting light source 17 shown in FIG. 1 so that they are driven by the same LD power source and emit pulse beams in synchronization with each other. The exciting laser beam and the near infrared laser beam emitted from the respective lasers are caused to travel along a common optical path to impinge upon the organic part 1 by use of a dichroic mirror or the like. One of the filters Mxy(2,1) and Mxy(1,2) which transmit only light in a wavelength range h2 of each micro-segment Mxy shown in FIGS. 5A and 5B is replaced with a filter which transmits only near infrared light and cuts the fluorescence (will be referred to as "near infrared filter", hereinbelow). Fluorescence Ke emitted from the organic part 1 upon excitation by the exciting light Le and the infrared light reflected at the organic part 1 are caused to form images on the end face Ki of the fluorescence image optical fiber 26 by the fluorescence image objective lens 4 and the images are propagated through the fluorescence image optical fiber 26 to the other end face Ko and then focused on the light receiving face of the high-sensitive image taking device 10 through the exciting light cut filter 24 and the mosaic filter with the exciting light contained in the fluorescence image removed by the cut filter 24. When intensities of fluorescence Ke or near infrared light Ir passing through the respective filters Mxy(1,1) (transmitting a wavelength range of h1), Mxy(2,1) (transmitting a wavelength range of h2), Mxy(2,2) (transmitting a wavelength range of h3) and Mxy(1,2) (near infrared filter) of one micro-segment Mxy are represented by Kh1, Kh2, Kh3 and Ih4, the fluorescence yield and the normalized intensity if fluorescence for the micro-segment Mxy are obtained according to the following formulae.

fluorescence yield=intensity of the overall fluorescence/intensity of reflected near infrared light=($Kh1+Kh2+Kh3$)/$Ih4$ normalized intensity=intensity of fluorescence in the wavelength range of $h2$/intensity of the overall fluorescence=$Kh2$/($Kh1+Kh2+Kh3$)

The fluorescence yield may be obtained by use of the intensity of exciting light reflected at the organic part 1 in place of the intensity of near infrared light reflected at the organic part 1. In this case, the exciting light cut filter 24 shown in FIG. 1 is removed and the filter Mxy(1,2) of each micro-segment Mxy of the mosaic filter is replaced with a filter which cuts the fluorescence and transmits only light near 410 nm. In this case, the near infrared light source need not be used.

On the basis of the fluorescence yield and the normalized intensity of the fluorescence thus obtained, the tissue condition of the organic part 1 is recognized in the same manner as described above.

The aforesaid threshold values and the contents of the logical operation are changed according to the purpose of diagnosis, e.g., according to the sex, age or the like of the patients or the kind of disease to be checked such as cancer, ulcer, inflammation, metaplasia or the like.

Though, in the embodiment described above, the fluorescence endoscope is provided with an image taking device for a normal image and an image taking device for a fluorescence image, the present invention can be applied to a fluorescence endoscope in which an image taking device such as a BT-CCD (back exposure CCD) is provided on the tip of the front end portion and a normal image and a fluorescence image are taken in sequence by switching a mosaic filter on the image taking device and illumination to which the organic part is exposed.

Further, the characteristic values may comprise those other than the intensity of the auto fluorescence, the normalized value of the intensity of the auto fluorescence, and fluorescence yield of the auto fluorescence, and may be three or more in number.

Further, though, in the embodiment described above, the characteristic values are binary-coded, they may be made three-or more valued. In this case, the logical operation should also be changed.

Further, though, in the embodiment described above, the present invention is applied to a fluorescence endoscope, the present invention can be applied to also other various fluorescence diagnosis system such as a microscope for operation, a colonoscope and the like.

In addition, all of the contents of Japanese Patent Application No. 11(1999)-195192 are incorporated into this specification by reference.

What is claimed is:

1. A fluorescence diagnosis system comprising
an exciting light projecting means which projects light onto an organic part to be observed exciting light which is in a predetermined wavelength range suitable for exciting intrinsic fluorophore of the organic part to emit auto fluorescence,
a detecting means which detects the intensity of the auto fluorescence emitted from the intrinsic fluorophore of the organic part to be observed upon excitation by the exciting light,
a characteristic value obtaining means which obtains a plurality of characteristic values from the intensity of the auto fluorescence detected by the detecting means, and
a recognizing means which recognizes the condition of the organic part observed on the basis of the characteristic values, in which the characteristic values comprise an intensity of the auto fluorescence and a normalized value of the intensity of the auto fluorescence, or a fluorescence yield of the auto fluorescence and a normalized value of the intensity of the auto fluorescence.

2. A fluorescence diagnosis system as defined in claim 1 in which the normalized value of the intensity of the auto fluorescence is obtained by dividing the intensity of a short wavelength component of the auto fluorescence by the intensity of the overall auto fluorescence.

3. A fluorescence diagnosis system as defined in claim 1 in which the recognizing means recognizes the condition of the organic part to be observed by making the characteristic values multivalued and executing a logical operation on the basis of the multivalued characteristics values.

4. A fluorescence diagnosis system as defined in claim 1 in which detection of the intensity of the auto fluorescence, obtaining the characteristic values and recognition of the condition of the organic part are carried out pixel by pixel.

5. The system of claim 4, wherein said recognizing means compares at least one of said plurality of characteristic values to a corresponding threshold value and subjects the result of the comparison to logical operations for recognizing the condition of the organic part.

6. The system of claim 4, wherein the recognition means sets a ratio of the characteristic values as a threshold, and comparing the intensity of auto-fluorescence to the ratio.

7. A fluorescence diagnosis method comprising:

projecting an exciting light onto an organic part to be observed, said exciting light suitable to excite said organic part to emit auto fluorescence;

detecting an intensity of the auto fluorescence emitted from the intrinsic fluorophore of the organic part upon excitation by the exciting light;

obtaining a plurality of characteristic values from the detected intensity of the auto fluorescence, including values for an intensity of the auto fluorescence over a wavelength range, a normalized value of the intensity of the auto fluorescence, and a fluorescence yield of the auto fluorescence; and recognizing the condition of the organic part on the basis of logical operations performed on said intensity of the auto fluorescence over the wavelength range and said normalized value of the intensity of the auto fluorescence, or on the basis of logical operations performed on said fluorescence yield of the auto fluorescence and said normalized value of the intensity of the auto fluorescence.

8. The method of claim 7, in which detecting the intensity of the auto fluorescence, obtaining said values, and recognizing the condition of the organic part are carried out pixel by pixel.

9. The method of claim 8, wherein recognizing the condition of the organic part comprises comparing at least one of said a plurality of characteristic values to a corresponding threshold value and subjecting the result of the comparison to logical operations for recognizing the condition of the organic part.

10. The method of claim 8, wherein recognition of the condition of the organic part comprises setting a ratio of the characteristic values as a threshold, and comparing the intensity of auto-fluorescence to the ratio.

* * * * *